(12) United States Patent
Robbins et al.

(10) Patent No.: US 8,747,863 B2
(45) Date of Patent: Jun. 10, 2014

(54) VACCINE FOR SHIGELLA

(75) Inventors: John B. Robbins, New York, NY (US); Rachel Schneerson, Bethesda, MD (US); Joanna Kubler-Kielb, Bethesda, MD (US); Christopher P. Mocca, Columbia, MD (US); Evguenii Vinogradov, Ottawa (CA)

(73) Assignees: The United States of America, as represented by the Secretary of the Department of Health and Human Services, Washington, DC (US); National Research Council of Canada, Ottawa (CA)

( * ) Notice: Subject to any disclaimer, the term of this patent is extended or adjusted under 35 U.S.C. 154(b) by 461 days.

(21) Appl. No.: 13/059,051

(22) PCT Filed: Aug. 14, 2009

(86) PCT No.: PCT/US2009/053897
§ 371 (c)(1),
(2), (4) Date: May 2, 2011

(87) PCT Pub. No.: WO2010/019890
PCT Pub. Date: Feb. 18, 2010

(65) Prior Publication Data
US 2011/0212125 A1 Sep. 1, 2011

Related U.S. Application Data

(60) Provisional application No. 61/089,394, filed on Aug. 15, 2008.

(51) Int. Cl.
*A61K 49/00* (2006.01)
*A61K 39/00* (2006.01)
*A61K 47/00* (2006.01)
*A61K 39/02* (2006.01)
*A61K 39/385* (2006.01)
*A61K 47/06* (2006.01)

(52) U.S. Cl.
CPC .............. *A61K 39/02* (2013.01); *A61K 39/385* (2013.01); *A61K 47/06* (2013.01)
USPC ....... 424/234.1; 424/9.1; 424/9.2; 424/184.1; 424/193.1; 424/197.11

(58) Field of Classification Search
CPC ..... A61K 39/00; A61K 39/02; A61K 39/385; A61K 47/00
USPC ................ 424/9.1, 9.2, 184.1, 193.1, 197.11, 424/234.1
See application file for complete search history.

(56) References Cited

FOREIGN PATENT DOCUMENTS

| WO | WO 99/03871 | 1/1999 |
| WO | WO 2005/003775 | 1/2005 |
| WO | WO 2008/013735 | 1/2008 |

OTHER PUBLICATIONS

Chu et al., "Preparation, characterization, and immunogenicity of conjugates composed of the O-specific polysaccharide of *Shigella dysenteriae* type 1 (Shiga's Bacillus) bound to tetanus toxoid," *Infection and Immunity* 59(12):4450-4458, Dec. 1, 1991.

Cohen et al., "Safety and immunogenicity of investigational *Shigella* conjugate vaccines in Israeli volunteers," *Infection and Immunity* 64(10):4074-4077, Oct. 1996.

Feng et al., "Structural and genetic characterization of the *Shigella boydii* type 13 O antigen," *Journal of Bacteriology* 186(2):383-392, Jan. 2004.

Kubler-Kielb et al., "A new method for conjugation of carbohydrates to proteins using an aminooxy-thiol heterobifunctional linker," *Journal of Organic Chemistry* 70(17):6987-6990, Aug. 19, 2005.

Kubler-Kielb et al., "Saccharide/protein conjugate vaccines for *Bordetella* species: Preparation of saccharide, development of new conjugation procedures, and hysic-chemical immunological characterization of the conjugates," *Vaccine* 26(29-30):3587-3593, Jul. 4, 2008.

Kubler-Kielb et al., "The elucidation of the structure of the core part of the LPS from *Plesiomonas shigelloides* serotype O17 expressing O-polysaccharide chain identical to the *Shigella sonnei* O-chain," *Carbohydrate Research* 343(18):3123-3127, Dec. 8, 2008.

Lees et al., "Versatile and efficient synthesis of protein-polysaccharide conjugate vaccines using aminooxy reagents and oxime chemistry,"*Vaccine* 24(6):716-729, Feb. 6, 2006.

Lin et al., "The Efficacy of a *Salmonella typhi* Vi Conjugate Vaccine in Two-to-Five-Year-Old Children," *The New England Journal of Medicine* 344(17):1263-1269, 2001.

(Continued)

*Primary Examiner* — Rodney P Swartz
(74) *Attorney, Agent, or Firm* — Klarquist Sparkman LLP

(57) ABSTRACT

Disclosed are immunogenic conjugates and therapeutic compositions that include such immunogenic conjugates. Also disclosed are methods of treating and/or inhibiting an *Shigella sonnei* infection. The disclosed immunogenic conjugates have the general structure:

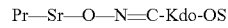

wherein Pr is a carrier protein, Sr is an optional spacer moiety, Kdo is an 3-deoxy-D-manno-octulosonic acid or a derivative thereof, and OS is an oligosaccharide or polysaccharide obtained from *S. sonnei*. In specific examples, the immunogenic conjugates include the core oligosaccharide obtained from *S. sonnei* having the structure:

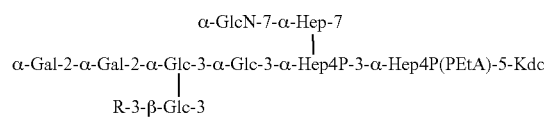

wherein R is between 1 and 10 disaccharide repeat units. In specific examples, the disaccharide repeat unit included in the immunogenic conjugate has the structure:

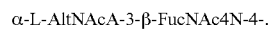

19 Claims, 8 Drawing Sheets

(56) References Cited

OTHER PUBLICATIONS

Molinaro et al., "Fully structural characterization of *Shigella flexneri* M90T serotype 5 wild-type R-LPS and its ΔgalU mutant: glycine residue location in the inner core of the lipopolysaccharide," *Glycobiology* 18(3):260-269, Jan. 3, 2008.

Passwell et al., "Safety and immunogenicity of improved *Shigella* O-specific polysaccharide-protein conjugate vaccines in adults in Israel," *Infection and Immunity* (60)3:1351-1357, Mar. 1, 2001.

Pavliakova et al., "*Clostridium difficile* recombinant toxin A repeating units as a carrier protein for conjugate vaccines: studies of pneumococcal type 14, *Escherichia coli* K1, and *Shigella flexneri* Type 2a polysaccharides in mice," *Infection and Immunity* 68(4):2161-2166, Apr. 1, 2000.

Pozsgay et al., "Protein conjugates of synthetic saccharides elicit higher levels of serum IgG lipopolysaccharide antibodies in mice than do those of the O-specific polysaccharide from *Shigella dysenteriae* type 1," *Proceedings of the National Academy of Sciences of U.S.A.* 96(9):5194-5197, Apr. 27, 1999.

Pozsgay et al., "Effect of the nonreducing end of *Shigella dysenteriae* type 1 O—specific oligosaccharides on their immunogenicity as conjugates in mice," *Proceedings of the National Academy of Sciences of the U.S.A.* 104(36):14478-14482, Sep. 4, 2007.

Robbins et al., "Hypothesis for Vaccine Development: Protective Immunity to Enteric Diseases Caused by Nontyphoidal Salmonellae and Shigellae May Be Conferred by Serum IgG Antibodies to the O-Specific Polysaccharide of Their Lipopolysaccharides," *Clinical Infections Diseases* 15:346-61, 1992.

Robbins et al., "Synthesis, characterization, and immunogenicity in mice of *Shigella sonnei* O-specific oligosaccharide-core-protein conjugates," *Proceedings of the National Academy of Sciences of the U.S.A.* 106(19):7974-7978, May 19, 2009.

Senchenkova et al., "Structural and genetic characterization of the *Shigella boydii* type 10 and type 6 O antigens," *Journal of Bacteriology* 187(7):2551-2554, Apr. 2005.

Schneerson et al., "Preparation, Characterization, and Immunogenicity of *Haemophilus infulenzae* type b Polysaccharide-Protein Conjugates," *Journal of Experimental Medicine* 152:361-376, 1980.

Taylor et al., "Synthesis, characterization, and clinical evaluation of conjugate vaccines composed of the O-specific polysaccharides of *Shigella dysenteriae* type 1, *Shigella flexneri* type 2a, and *Shigella sonnei* (*Plesiomonas shigelloides*) bound to bacterial toxoids," *Infection and Immunity* 61(9):3678-3687, Sep. 1993.

Wang et al., "Sequence analysis of four *Shigella boydii* O-antigen loci: Implication for *Escherichia coli* and *Shigella* relationships," *Infection and Immunity* 69(11):6923-6930, Nov. 2001.

Xu et al., "Molecular cloning and characterization of genes for *Shigella sonnei* form I O polysaccharide: proposed biosynthetic pathway and stable expression in a live *Salmonella* vaccine vector," *Infection and Immunity* 70(8):4414-4423, Aug. 2002.

International Search Report from PCT Application No. PCT/US2009/053897 dated Apr. 2, 2010.

Written Opinion of the International Search Report from PCT Application No. PCT/US2009/053897 dated Apr. 2, 2010.

FIG. 5

Table 1. NMR analyses of *S. sonnei* O-SPC fragment ($\delta$, ppm)

| Residue, compound | Nucleus | 1 | 2 | 3 | 4 | 5 | 6a | 6b |
|---|---|---|---|---|---|---|---|---|
| α-Glc H | H | 5.28 | 3.68 | 4.06 | 3.79 | 3.86 | | |
| | C | 101.6 | 71.6 | 77.4 | 71.6 | 73.4 | | |
| α-Glc K | H | 5.83 | 3.89 | 4.19 | 3.58 | 4.13 | 3.75 | 3.75 |
| | C | 95.7 | 73.8 | 79.0 | 69.0 | 72.5 | 62.3 | |
| α-Gal L | H | 5.62 | 3.99 | 4.21 | 4.01 | 4.13 | | |
| | C | 92.5 | 73.5 | 69.3 | 70.4 | 72.4 | | |
| α-Gal M | H | 5.33 | 3.86 | 3.98 | 4.00 | 4.12 | | |
| | C | 96.7 | 69.4 | 70.5 | 70.5 | 72.5 | | |
| β-Glc T | H | 4.74 | 3.40 | 3.70 | 3.50 | 3.45 | 3.78 | 3.90 |
| | C | 103.7 | 74.0 | 85.4 | 69.3 | 76.7 | 61.4 | |
| β-FucNAc4N W | H | 4.77 | 3.84 | 4.19 | 3.86 | 4.08 | 1.34 | |
| | C | 102.8 | 52.6 | 77.0 | 55.9 | 68.3 | 16.7 | |
| α-AltNAcA X | H | 4.79 | 3.84 | 3.76 | 4.47 | 4.60 | 174.7 | |
| | C | 102.3 | 52.4 | 68.9 | 78.3 | 78.1 | | |
| β-FucNAc4N Y | H | 4.76 | 3.88 | 4.19 | 3.96 | 4.08 | 1.34 | |
| | C | 104.2 | 52.1 | 77.0 | 56.1 | 68.3 | 16.7 | |
| α-AltNAcA Z | H | 4.90 | 4.00 | 3.69 | 4.40 | 4.52 | 175.1 | |
| | C | 102.1 | 52.5 | 69.1 | 69.9 | 78.4 | | |

FIG. 6

Table 2. Composition and GM of serum IgG anti-S. sonnei LPS induced by O-SPC conjugates bound to BSA or rDT and by full-length O-SP bound to rEPA

| No. | Conjugate | Molecular mass of conjugate, kDa | Molecular mass of sugar part, kDa | No. O-SPC chains per protein molecule | IgG, EU Anti-LPS | | IgG, EU Anti-rDT | | |
|---|---|---|---|---|---|---|---|---|---|
| | | | | | Second injection | Third injection | Second injection | Third injection | |
| 1 | BSA/O-SPC-F2* | 93.1 | 22.2 | 7 | 79 | 366 | ND | ND | |
| 2 | rDT/O-SPC-F2 | 80.6 | 18.5 | 5 | 5 | 392 | 2 | 91 | |
| 3 | rDT/O-SPC-F2 | 99.5 | 37.4 | 12 | 11 | 150 | 0.1 | 2 | |
| 4 | BSA/O-SPC-F3† | 95.2 | 24.3 | 11 | ND | ND | ND | ND | |
| 5 | rEPA/O-SP‡ | ND | ND | ND | 11 | 67 | ND | ND | |

Mice (10 per group) were injected with 2.5 μg per mouse of saccharide as a conjugate, 3 times, 2 weeks apart and bled 1 week after the last two injections. ND, not determined.
*S. sonnei O-SPC-F2 = core + average 3.5 RU of O-SP; average molecular mass = 3,206 Da.
†S. sonnei O-SPC-F3 = core + average 1.3 RU of O-SP; average molecular mass = 2,311 Da.
‡S. sonnei O-SP = core + average 29 RU of O-SP bound by multipoint attachment.

FIG. 7

Table 3. Competitive inhibition of antisera induced by
BSA/O-SPC-F2 and by rPA/O-SP conjugates to the *S. sonnei* LPS,
by different inhibitors

|  |  | Inhibition, % | |
|---|---|---|---|
| Inhibitor | Amount, µg | Anti-*S. sonnei* BSA/O-SPC | Anti-*S. sonnei* rPA/O-SP |
| *S. sonnei* O-SP | 50 | 100 | 100 |
| *S. sonnei* O-SP | 10 | 100 | 100 |
| *S. sonnei* O-SP | 2 | 95 | 95 |
| *P. shigelloides* O-SP | 50 | 100 | 100 |
| *P. shigelloides* O-SP | 10 | 100 | 100 |
| *P. shigelloides* O-SP | 2 | 96 | 94 |
| *P. shigelloides* O-SP $_{\text{no core}}$* | 50 | 100 | 100 |
| *P. shigelloides* O-SP $_{\text{no core}}$ | 10 | 100 | 100 |
| *P. shigelloides* O-SP $_{\text{no core}}$ | 2 | 92 | 90 |
| *S. sonnei* O-SPC-F2 | 50 | 100 | 100 |
| *S. sonnei* O-SPC-F2 | 10 | 81 | 84 |
| *S. sonnei* O-SPC-F2 | 2 | 10 | 19 |
| Hla CPS+ | 50 | 0 | 0 |
| Hla CPS | 10 | 0 | 0 |
| Hla CPS | 2 | 0 | 0 |

O-SP indicates high molecular mass saccharide (core + average 29 O-SP RU).
O-SPC-F2 indicates low molecular mass saccharide (core + average. 3.5 O-SP RU).
*Core was hydrolyzed by anhydrous HF (see Materials and Methods).
+Hla CPS indicates *H. influenzae* type a capsular polysaccharide as control.

FIG. 8

Table 4

| No | Conjugate | Protein concentr [mg/ml] | Sugar concentr [mg/ml] | Ratio Pr:Sug [wt:wt] | No. of O-SPC chains per Pr | IgG [EU] anti-LPS 2nd inj. | IgG [EU] anti-LPS 3rd inj. | IgG [EU] anti-Protein 2nd inj. | IgG [EU] anti-Protein 3rd inj. |
|---|---|---|---|---|---|---|---|---|---|
| 1 | BSA/O-SPC-F2[1] | 2.5 | 0.8 | 1:0.32 | 7 | 79 | 366 | na | |
| 2 | DT/O-SPC-F2 | 2.0 | 0.7 | 1:0.35 | 6 | 5 | 392 | 2 | 91 |
| 3 | DT/O-SPC-F2 | 2.1 | 1.2 | 1:0.57 | 12 | 11 | 150 | 0.1 | 2 |
| 5 | DT/O-SPC-F2 | 2.3 | 0.7 | 1:0.30 | 6 | 19 | 328 | 1 | 11 |
| 6 | rBRU/O-SPC-F2 | 1.9 | 0.6 | 1:0.33 | 6 | 26 | 593 | 2 | 136 |
| 7 | rBRU/O-SPC-F2 | 2.4 | 1.0 | 1:0.40 | 8 | na | 284 | na | 117 |
| 8 | rBRU/O-SPC-F2 | 3.7 | 1.6 | 1:0.43 | 8 | na | 691 | na | 276 |
| 9 | rBRU/O-SPC-F2 | 2.8 | 1.8 | 1:0.64 | 12 | na | 295 | na | 84 |
| 10 | rBRU/O-SPC-F2 | 2.1 | 1.2 | 1:0.57 | 10 | na | 896 | na | 110 |
| 11 | rBRU/O-SPC-F2 | 3.8 | 1.1 | 1:0.30 | 6 | na | 200 | na | 86 |
| 4 | BSA/O-SPC-F3[2] | 4.7 | 2.2 | 1:0.47 | 10 | na | | na | | na= not analyzed; [1] *S. sonnei* O-SPC-F2 = core + avr. 3.5 RU of O-SP; avr. Mm = 3206 Da, [2] *S. sonnei* O-SPC-F3 = core + av. 1.3 RU of O-SP; av. Mm = 2311 Da;

US 8,747,863 B2

VACCINE FOR SHIGELLA

CROSS REFERENCE TO RELATED APPLICATIONS

This is the U.S. National Stage of International Application No. PCT/US2009/053897, filed Aug. 14, 2009, which was published in English under PCT Article 21(2), which in turn claims the benefit of U.S. Provisional Application No. 61/089,394, filed Aug. 15, 2008. The provisional application is incorporated herein in its entirety.

FIELD

Disclosed herein are immunogenic conjugates made from oligosaccharide or polysaccharide antigens obtained from *Shigella sonnei* and methods of treatment using such conjugates.

BACKGROUND

Shigellae are Gram-negative bacteria, pathogens to humans only, that can cause endemic and epidemic dysentery worldwide, especially in the developing countries. It has been estimated that ≈160 million cases of shigellosis with ≈1 million deaths occurring worldwide annually. At least half of the cases and deaths are believed to occur in children <5 years old. Control of this disease is hampered by the low infectious dose of this pathogen (<100 bacteria) and lack of safe drinking water and food in the developing world. The symptoms usually start with watery diarrhea that later develops into dysentery, characterized by high fever, blood and mucus in the stool, and cramps.

Lipopolysaccharides (LPSs) of *Shigella* are both essential virulence factors and protective antigens of this genus. The outer domain of this tripartite molecule, termed O-specific polysaccharide (O-SP), "shields" the bacteria from serum complement killing, similar to the action of capsular polysaccharides. It has been hypothesized that serum antibodies to the O-SP of shigellae confer immunity to humans against the homologous bacteria. To test this hypothesis, experimental vaccines composed of protein conjugates of the O-SP of *Shigella dysenteriae* type 1, *Shigella sonnei*, and *Shigella flexneri* 2a were synthesized and evaluated in young adults. Evaluation of a *S. sonnei* O-SP/recombinant *Pseudomonas aeruginosa* Exotoxin A (rEPA) conjugate in Israeli soldiers demonstrated 72% efficacy with vaccine failures occurring in individuals who responded with significantly lower serum antibody levels than those who were protected. Evaluation of such conjugates in children showed age-related antibody responses and protection. A significant improvement in the immunogenicity of *S. dysenteriae* type 1 conjugates was achieved by using synthetic oligosaccharides (OS) of defined lengths bound by their reducing ends to a protein at defined densities. Unfortunately, this improvement could not be replicated for *S. sonnei*, as synthesis of *S. sonnei* O-SP oligosaccharides has not been possible to date. Thus, the need still exists for improved *S. sonnei* specific vaccines. The conjugates and methods of treatment disclosed herein meet those needs.

SUMMARY

Disclosed are immunogenic conjugates and therapeutic compositions that include such immunogenic conjugates. The disclosed immunogenic conjugates have the general structure:

$$Pr-Sr-O-N=C-Kdo-OS$$

wherein Pr is a carrier protein, Sr is an optional spacer moiety, Kdo is 3-deoxy-D-manno-octulosonic acid or a derivative thereof, and OS is an oligosaccharide or polysaccharide obtained from *S. sonnei*. The disclosed immunogenic conjugate can include a core oligosaccharide obtained from *S. sonnei*. In specific examples, the core oligosaccharide obtained from *S. sonnei* has the structure:

$$\alpha\text{-GlcN-7-}\alpha\text{-Hep-7}$$
$$|$$
$$\alpha\text{-Gal-2-}\alpha\text{-Gal-2-}\alpha\text{-Glc-3-}\alpha\text{-Glc-3-}\alpha\text{-Hep4P-3-}\alpha\text{-Hep4P(PEtA)-5-Kdc}$$
$$|$$
$$R\text{-3-}\beta\text{-Glc-3}$$

wherein R is between 1 and 10 disaccharide repeat units. In some examples, the disaccharide repeat unit included in the immunogenic conjugate has the structure:

$$\alpha\text{-L-AltNAcA-3-}\beta\text{-FucNAc4N-4-}.$$

Also disclosed are methods of treating and/or inhibiting an infection by *S. sonnei* in a subject. These methods include by administering to a subject the disclosed immunogenic conjugates, for example by eliciting an immune response in a subject to *S. sonnei*

BRIEF DESCRIPTION OF THE DRAWINGS

FIG. 5 is the table referred to herein as Table 1.
FIG. 6 is the table referred to herein as Table 2.
FIG. 7 is the table referred to herein as Table 3.
FIG. 8 is the table referred to herein as Table 4. Composition and GM of serum IgG anti-*S. sonnei* LPS (Elisa Units, EU) induced by conjugates of O-SPC bound to bovine serum albumin (BSA), a recombinant diphtheria toxin (non toxic) (rDT) or a recombinant *C. difficile* toxin B repeat (rBRU). Mice (10 per group) were injected with 2.5 µg of saccharide as a conjugate per mouse, 3 times, 2 weeks apart and bled one week after the last two injections.

DETAILED DESCRIPTION

I. Abbreviations

Figure 1:
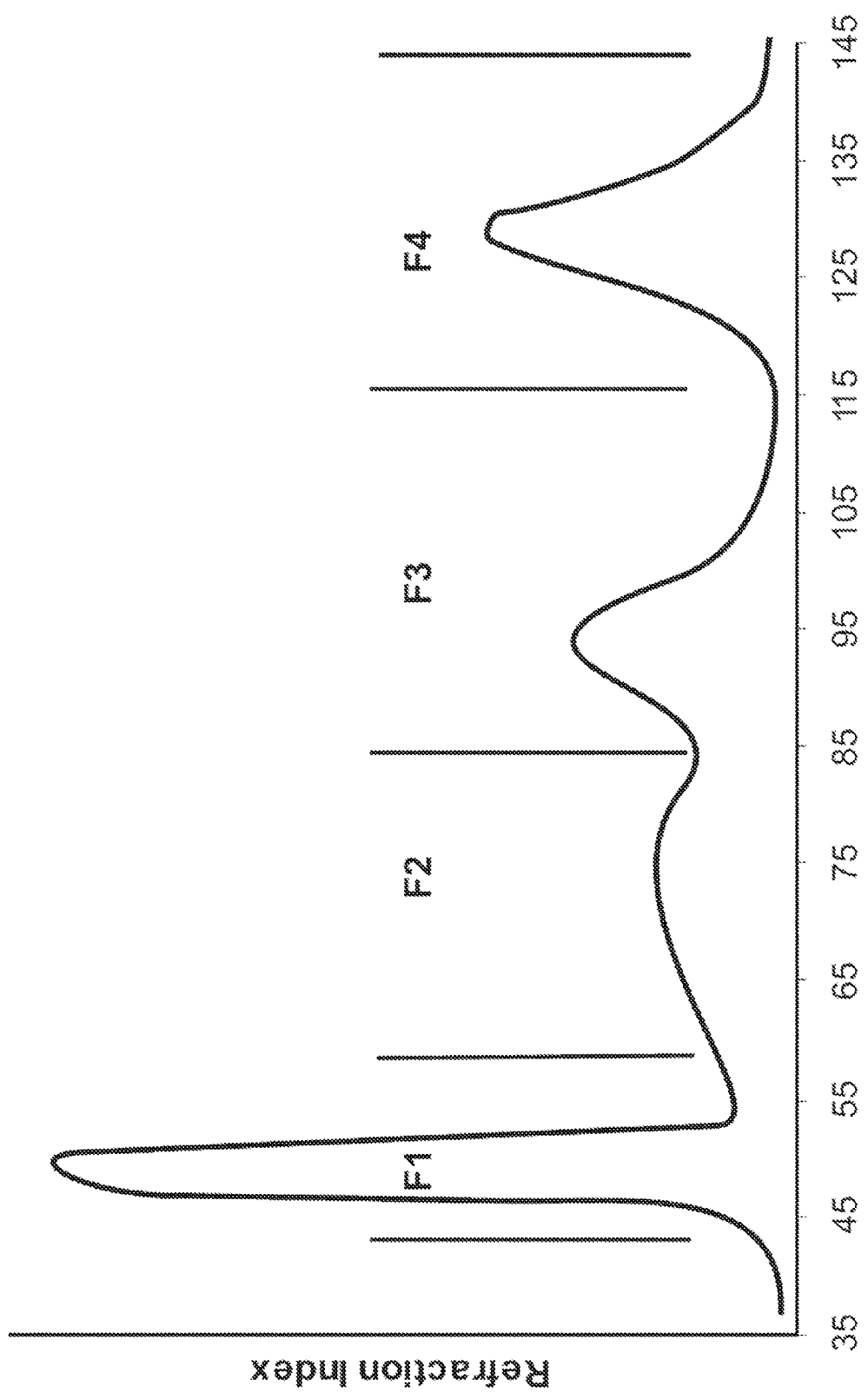
FIG. 1 is a trace of an exemplary refraction spectra obtained from the elution from a BIOGEL® P-10 gel filtration column of *S. sonnei* LPS after 1% acetic acid hydrolysis. F1-F4 refer to the elution fractions. F1, O-SP, ≈1 RU (Repeat Units); F2, core+average 3.5 RU of O-SP; F3, core+average 1.3 RU of O-SP; F4, degradation products, no core or O-SP.

ADH: adipic acid dihydrazide
AT: anthrax toxin
ATR: anthrax toxin receptor
EDAC: 1-ethyl-3-(3-dimethylaminopropyl)carbodiimide-HCl
EF: edema factor
GLC-MS: gas-liquid chromatography-mass spectrometry
kDa: kilodaltons
LC-MS: liquid chromatography-mass spectrometry
LeTx: lethal toxin
LF: lethal factor
LOS: lipooligosaccharide
LPS: lipopolysaccharide
MALDI-TOF: matrix-assisted laser desorption ionization time-of-flight
OS: oligosaccharide
μg: microgram
μl: microliter
PA: protective antigen
PBS: phosphate buffered saline
SBAP: succinimidyl 3-(bromoacetamido)propionate
SFB: succinimidylformylbenzoate
SPDP: N-hydroxysuccinimide ester of 3-(2-pyridyl dithio)-propionic acid
SLV: succinimidyllevulinate
TT: tetanus toxoid The saccharide units disclosed herein are abbreviated as below following conventional oligosaccharide/polysaccharide nomenclature:

AltNAcA: N-Acetyl-L-altrosaminuronic acid
anhKdo: anhydro Kdo
Fuc: fucose
FucNAc4N: 2-acetamido-4-amino-2,4,6-trideoxy-galactose
Gal: galactose
Glc: glucose,
GlcN: glucosamine
GlcNAc: N-acetylglucosamine
GalNAc: N-acetylgalactosamine
Hep: glycero-D-manno-heptopyranoside (heptose)
Hex: hexose
Man: mannose

II. Listing of Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references. In case of conflict, the present specification, including explanations of terms, will control.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. In addition, the materials, methods, and examples are illustrative only and not intended to be limiting.

To facilitate review of the various examples of this disclosure, the following explanations of specific terms are provided:

Adjuvant: A substance that enhances the immune response to an antigen. Development of vaccine adjuvants for use in humans is reviewed in Singh et al. (*Nat. Biotechnol.* 17:1075-1081, 1999), which discloses that, at the time of its publication, aluminum salts, such as aluminum hydroxide (Amphogel, Wyeth Laboratories, Madison, N.J.), and the MF59 microemulsion are the only vaccine adjuvants approved for human use. An aluminum hydrogel (available from Brentg Biosector, Copenhagen, Denmark) is a adjuvant.

In one embodiment, an adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CpG oligodeoxynucleotides, as described in U.S. Pat. Nos. 6,194,388; 6,207,646; 6,214,806; 6,218,371; 6,239,116; 6,339,068; 6,406,705; and 6,429,199.

Administration: The introduction of a composition into a subject by a chosen route. For example, if the chosen route is intranasal, the composition is administered by introducing the composition into the nose of the subject.

Animal: A living multi-cellular vertebrate or invertebrate organism, a category that includes, for example, mammals and birds. The term mammal includes both human and non-human mammals. Similarly, the term "subject" includes both human and veterinary subjects, such as non-human primates. Thus, administration to a subject can include administration to a human subject. Particular examples of veterinary subjects include domesticated animals (such as cats and dogs) and laboratory animals (for example, mice, rabbits, rats, gerbils, guinea pigs, and non-human primates)

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

Antigen: A compound, composition, or substance that can stimulate the production of antibodies or a T-cell response in a mammal, including compositions that are injected, absorbed or otherwise introduced into a mammal. Antigens can be any type of biologic molecule including, for example, simple intermediary metabolites, sugars (e.g., oligosaccharides, such as oligosaccharides obtained from *S. sonnei*), lipids, and hormones as well as macromolecules such as complex carbohydrates (e.g., polysaccharides), phospholipids, nucleic acids and proteins. In some examples, antigens include an oligosaccharide derived from *S. sonnei*.

Carrier: Any clinically acceptable protein to which an antigen such as an oligosaccharide or polysaccharide can be bound. When bound to a carrier, the bound molecule may become more immunogenic. In some examples, multiple antigens, for example multiple copies of a single antigen are bound to a carrier protein, for example in a "sun" configuration in which the antigens radiate away from the center carrier protein. In other examples, multiple copies of an antigen are bound to the carrier protein in the 'lattice configuration." Carriers are chosen to increase the immunogenicity of the bound molecule and/or to elicit antibodies against the carrier which are diagnostically, analytically, and/or therapeutically beneficial. Covalent linking of a molecule to a carrier confers enhanced immunogenicity and T-cell dependence (Pozsgay et al., *PNAS* 96:5194-97, 1999; Lee et al., *J. Immunol.* 116: 1711-18, 1976; Dintzis et al., *PNAS* 73:3671-75, 1976). Useful carriers include polymeric carriers, which can be natural (for example, proteins from bacteria or viruses), semi-synthetic or synthetic materials containing one or more functional groups to which a reactant moiety can be attached.

Examples of bacterial products for use as carriers include bacterial toxins, such as *B. anthracis* PA, LF and LT, and other bacterial toxins and toxoids, such as tetanus toxin/toxoid, diphtheria toxin/toxoid, *P. aeruginosa* exotoxin/toxoid/, pertussis toxin/toxoid, and *Clostridium perfringens* exotoxin/toxoid, recombinant diphtheria toxin (rDT) and *Clostridium difficile* toxin B repeat (rBRU). Viral proteins, such as hepatitis B surface antigen and core antigen can also be used as carriers.

Covalent Bond: An interatomic bond between two atoms, characterized by the sharing of one or more pairs of electrons by the atoms. The terms "covalently bound" or "covalently linked" refer to making two separate molecules into one contiguous molecule. The terms include reference to joining an antigen (such as an oligosaccharide obtained from *S. sonnei*) indirectly to a carrier molecule, with an intervening linker molecule.

Epitope: An antigenic determinant These are particular chemical groups or contiguous or non-contiguous peptide sequences or saccharide units on a molecule that are antigenic, that is, that elicit a specific immune response. An antibody binds a particular antigenic epitope based on the three dimensional structure of the antibody and the matching (or cognate) epitope.

Immune Response: A response of a cell of the immune system, such as a B-cell, T-cell, macrophage or polymorphonucleocyte, to a stimulus. An immune response can include any cell of the body involved in a host defense response. An immune response includes, but is not limited to, an adaptive immune response or inflammation. In some examples, an immune response is stimulated by administering to a subject a vaccine and/or disclosed immunogenic conjugate.

Immunogenic Conjugate or Composition: A term used herein to mean a composition useful for stimulating or eliciting a specific immune response (or immunogenic response) in a vertebrate. In some embodiments, the immunogenic response is protective or provides protective immunity, in that it enables the vertebrate animal to better resist infection or disease progression from the organism against which the immunogenic composition is directed, for example *S. sonnei*.

One specific example of a type of immunogenic composition is a vaccine.

Immunogen: A compound, composition, or substance which is capable, under appropriate conditions, of stimulating the production of antibodies in an animal, including compositions that are injected or absorbed into an animal. In some examples, an immunogen is an oligosaccharide obtained from *S. sonnei*.

Immunologically Effective Dose: An immunologically effective dose of the oligosaccharide-protein or polysaccharide-protein conjugates of the disclosure is therapeutically effective and will prevent, treat, lessen, or attenuate the severity, extent or duration of a disease or condition, for example, infection by *S. sonnei*.

Inhibiting or Treating a Disease: Inhibiting the full development of a disease or condition, for example, in a subject who is at risk for a disease such as *S. sonnei* infection. "Treatment" refers to a therapeutic intervention that ameliorates a sign or symptom of a disease or pathological condition after it has begun to develop. The term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" biological component (such as a lipopolysaccharide) has been substantially separated or purified away from other biological components in the cell of the organism in which the component naturally occurs, such as other chromosomal and extra-chromosomal DNA and RNA, proteins, glycolipids and organelles. Isolated does not require absolute purity, and can include protein or peptide molecules that are at least 50% isolated, such as at least 75%, 80%, 90%, 95%, 98%, 99%, or even 100% isolated.

Lipopolysaccharide (LPS): LPS is an endotoxin that is a major suprastructure of the outer membrane of Gram-negative bacteria which contributes greatly to the structural integrity of the bacteria, and protects them from host immune defenses. LPS typically contains three components: (a) Lipid A (a hydrophobic domain that typically consists of a glucosamine disaccharide that is substituted with phosphate groups and long chain fatty acids in ester and amide linkages); (b) a core polysaccharide or oligosaccharide that can include, for example, heptose, glucose, galactose and N-acetylglucosamine units depending upon the genera and species of bacteria; and (c) optionally, polysaccharide distal or side chain(s) (often referred to as the "O antigen" that can include, for example, mannose, galactose, D-glucose, N-acetylgalactosamine, N-acetylglucosamine, L-rhamnose, and a dideoxyhexose depending upon the genera and species of bacteria). Lipid A and the core polysaccharide or oligosaccharide domains are joined together by one or more units of 3-deoxy-D-manno-octulosonic acid ("Kdo", also known as ketodeoxyoctonate). A lipooligosaccharide (LOS) (also known as a "short chain LPS") commonly refers to an LPS that contains Lipid A plus a core polysaccharide or oligosaccharide. As used herein, the term LPS can include short chain LPS and LOS.

Oligosaccharide (OS): The term "oligosaccharide" is not necessarily restricted to a molecule having a specific number of saccharide units. However, in general, an oligosaccharide is a carbohydrate that contains from about 3 to about 20 simple sugars (e.g., monosaccharides) linked together. O-specific oligosaccharide+core (O-SPC) refers to an O-specific oligosaccharide chain attached to a core oligosaccharide or polysaccharide chain.

Pharmaceutical agent: A chemical compound or composition capable of inducing a desired therapeutic or prophylactic effect when properly administered to a subject.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the proteins and other compositions herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions, powder, pill, tablet, or capsule forms, conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Purified: The term "purified" does not require absolute purity; rather, it is intended as a relative term. Thus, for example, a purified peptide, protein, conjugate, LPS, or other active compound is one that is isolated in whole or in part from proteins, lipids or other contaminants. Generally, substantially purified peptides, proteins, conjugates, LPSs or other active compounds for use within the disclosure comprise more than 60% of all macromolecular species present in a preparation prior to admixture or formulation of the peptide, protein, conjugate, LPS or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, conjugate, LPS or other active compound is purified to represent greater than 70%, often greater than 90% of all macromolecular species present in a purified preparation prior to admixture with other formulation ingredients. In other cases, the purified preparation may be essentially homogeneous, wherein other macromolecular species are not detectable by conventional techniques.

Therapeutically effective amount: A quantity of a specific substance (for example, this may be the amount of an *S. sonnei* O-SPC-protein or polysaccharide-protein conjugate useful in increasing resistance to, preventing, ameliorating, and/or treating infection and disease caused by *S. sonnei*) sufficient to achieve a desired effect in a subject being treated. Ideally, a therapeutically effective amount of an agent is an amount sufficient to increase resistance to, prevent, ameliorate, and/or treat infection and disease caused by *S. sonnei* infection in a subject without causing a substantial cytotoxic effect in the subject. The effective amount of an agent useful for increasing resistance to, preventing, ameliorating, and/or treating infection and disease caused by *S. sonnei* infection in a subject will be dependent on the subject being treated, the severity of the affliction, and the manner of administration of the therapeutic composition. For example, a therapeutically effective amount of composition can vary from about 0.01 mg/kg body weight to about 1 g/kg body weight. When administered to a subject, a dosage will generally be used that will achieve target concentrations shown to achieve a desired in vivo effect.

*Shigella*: A genus of Gram-negative, non-spore forming rod-shaped bacteria closely related to *Escherichia coli* and *Salmonella*. The causative agent of human shigellosis, *Shigella* cause disease in primates, but not in other mammals. *Shigella* species are classified by four serogroups:

Serogroup A: *S. dysenteriae* (12 serotypes)
Serogroup B: *S. flexneri* (6 serotypes)
Serogroup C: *S. boydii* (23 serotypes)
Serogroup D: *S. sonnei* (1 serotype)

Group A-C are physiologically similar; *S. sonnei* (group D) can be differentiated on the basis of biochemical metabolism assays. Three *Shigella* groups are the major disease-causing species: *S. flexneri* is the most frequently isolated species worldwide and accounts for 60% of cases in the developing world; *S. sonnei* causes 77% of cases in the developed world, compared to only 15% of cases in the developing world; and *S. dysenteriae* is usually the cause of epidemics of dysentery, particularly in confined populations such as refugee camps.

Toxoid: A nontoxic derivative of a bacterial exotoxin produced, for example, by formaldehyde or other chemical treatment. Toxoids are useful in the formulation of immunogenic compositions because they retain most of the antigenic properties of the toxins from which they were derived.

Vaccine: A vaccine is a pharmaceutical composition that elicits a prophylactic or therapeutic immune response in a subject. In some cases, the immune response is a protective response. Typically, a vaccine elicits an antigen-specific immune response to an antigen of a pathogen, for example, a bacterial viral pathogen.

III. Description of Several Embodiments

This disclosure relates to conjugates for use in eliciting an immune response to *S. sonnei* and methods of using such conjugates for treating and/or inhibiting *S. sonnei* infection, for example by eliciting an immune response targeting *S. sonnei* oligosaccharides. To enhance antibody responses of subject, such as young children, to *S. sonnei* O-SP, and based on the (statistically significant) higher antibody levels induced by the synthetic *S. dysenterie* type 1 "sun" configuration conjugates than those induced by the full-length bacterial lattice-type conjugates disclosed herein are sun configuration *S. sonnei* conjugates. Because the synthesis of *S. sonnei* O-SP-based oligosaccharides could not be extended beyond a disaccharide unit prior to this disclosure, it was previously not possible to produce such conjugates.

To overcome this problem, low-molecular mass oligosaccharides containing LPS core plus several O-SP repeat units (RU) (referred to herein as O-SPC) from the bacterial LPS of *S. sonnei* were isolated and used for conjugate preparation. In one example, an oligosaccharide fraction, F2 containing the core plus an average of 3.5 repeat units RU of O-SP, was bound to the protein carriers by oxime formation. Examples of methods of conjugating oligosaccharides can be found in International Patent Application No. PCT/US2007/016373, which is incorporated herein by reference in its entirety.

The disclosed conjugates were antigenic and induced significantly higher IgG antibody levels than those induced by conjugates prepared with full-length O-SP. The antibodies induced by the O-SPC conjugate were directed to the RU of the O-SP and not to the core region based on the similar antibody levels obtained by using *S. sonnei* or *P. shigelloides*

LPS for ELISA and the close to a 100% inhibition of O-SPC-induced antibodies by O-SP of both organisms. The finding that the identity of the sugar residue positioned at the nonreducing end of the synthetic *S. dysenterie* type 1 oligosaccharide conjugates is an important variable for the immunogenicity of these conjugates and may be one reason for the superior immunogenicity of the O-SPC and synthetic oligosaccharide conjugates over O-SP conjugates; the former have more end groups.

A. Conjugate Vaccines

Disclosed herein are immunogenic conjugates that are formed from the core oligosaccharide obtained from *S. sonnei* and carrier protein. The immunogenic conjugates have the general structure:

Pr—Sr—O—N═C-Kdo-OS (I)

in which Pr represents carrier protein, Sr is an optional spacer moiety, Kdo is 3-deoxy-D-manno-octulosonic acid or a derivative thereof, and OS is an oligosaccharide or polysaccharide obtained from *S. sonnei* LPS. In some embodiments, the immunogenic conjugate includes a core oligosaccharide from *S. sonnei*. Exemplary methods of obtaining a core oligosaccharide from *S. sonnei* are given below in the examples, although other suitable methods, such as those detailed in this section can be used.

In some embodiments, the oligosaccharide core comprises or consists of:

(II)

α-GlcN-7-α-Hep-7
|
α-Gal-2-α-Gal-2-α-Glc-3-α-Glc-3-α-Hep4P-3-α-Hep4P(PEtA)-5-Kdo
|
R-3-β-Glc-3 wherein R is between 1 and 10 disaccharide repeat units, such as about 1, about 2, about 3, about 4, about 5, about 6, about 7, about 8, about 9, or about 10 disaccharide repeat units. In some examples, the disaccharide repeat unit comprises or consists of the structure:

α-L-AltNAcA-3-β-FucNAc4N-4-. (III)

The linkage between the oligosaccharide core (II) and the disaccharide repeat (III) is between the Glc-3 and the FucNAc4N moieties shown above in bold.

In some embodiments, multiple O-PSCs are conjugated to a single protein carrier molecule. For example, the number of oligosaccharide chains bound to a single protein carrier molecule may vary depending upon the specific O-SPC and the carrier protein, but in general, about 1 to about 20, such as about 1, about 2, about 3, about 4, about 5, about 6, about 7, about 8, about 9, about 10, about 11, about 12, about 13, about 14, about 15, about 16, about 17, about 18, about 19, about 20 or even more than 20 O-SPC chains can be bound to each protein carrier molecule, for example about 1 to about 5, about 3 to about 7, about 5 to about 9, about 7 to about 12, about 9 to about 15, about 13 to about 17 or even about 15 to about 20 O-SPC chains can be bound to each protein carrier molecule.

Specific, non-limiting examples of water soluble protein carriers that can be conjugated to O-SPC obtained from *S. sonnei* include, but are not limited to, natural, semi-synthetic or synthetic polypeptides or proteins from bacteria or viruses. In some examples, bacterial products for use as carriers include bacterial wall proteins and other products (for example, streptococcal or staphylococcal cell walls), and soluble antigens of bacteria. In another examples, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GENBANK® as Accession No. NC 007322 as available Aug. 15, 2008, herein incorporated by reference), including variants that share at least 90%, at least 95%, or at least 98% amino acid sequence homology to PA, fragments that contain at least one antigenic epitope, and analogs or derivatives capable of eliciting an immune response; *B. anthracis* LF (for example, as encoded by the complement of bases 149357 to 151786 of GENBANK® Accession No. NC 007322 as available Aug. 15, 2008, herein incorporated by reference); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065); *P. aeruginosa* exotoxin/toxoid/ (for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); *C. difficile* toxin B (for example, as available of GENBANK® Accession No. CAA43299, AAO83645, AAO83646, CAC19891 as available Aug. 15, 2008, herein incorporated by reference); and *C. perfringens* exotoxin/toxoid (for example, as described in U.S. Pat. Nos. 5,817,317 and 6,403,094). Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin, horseshoe crab hemocyanin, edestin, mammalian serum albumins, and mammalian immunoglobulins. In specific examples, a disclosed immunogenic conjugate includes a recombinant diphtheria toxin (rDT). In other examples, a disclosed immunogenic conjugate includes a recombinant aeruginosa Exotoxin A (rEPA). In still other examples, a disclosed immunogenic conjugate includes a recombinant *C. difficile* toxin B repeat (rBRU).

Methods for conjugating oligosaccharides or polysaccharides having a 3-deoxy-D-manno-octulosonic acid moiety located at the terminal reducing end of the oligosaccharides or polysaccharides can be found in International Patent Application No. PCT/US2007/016373, which is incorporated herein by reference in its entirety. According to these methods, binding the oligosaccharide by Kdo at the reducing end of the oligosaccharide means that all of the conserved oligosaccharide structure remains intact or unmodified (e.g., none of the saccharide residues are oxidized). The conjugates disclosed herein preserve the external non-reducing end of the oligosaccharide, are recognized by antisera, and induce antibody responses in mice.

The oligosaccharide may be obtained from *S. sonnei*, as well as to other enterobacteriacea and other gram-negative bacteria having Kdo molecule between Lipid A and oligo/polysaccharide chain of their LPS. The oligosaccharides or polysaccharides that are conjugated include a general structure of:

O-chain-core OS-Kdo (IV)

The Kdo moiety (or derivative thereof) is the moiety that results after acid hydrolysis treatment of the isolated LOS or LPS. In some examples the acid hydrolysis treatment results in the formation of anhydro-Kdo as described in more detail below and it has a structure represented by (anhydro-Kdo could also be referred to as 4, 8(7)-anhydro derivative of Kdo):

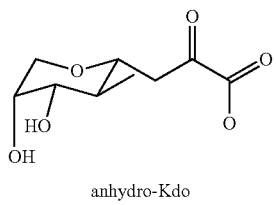

anhydro-Kdo

The oligosaccharide or polysaccharide typically is derived from LPS present in *S. sonnei*. The LPS initially is isolated from the other constituents of the bacteria cell structure. Illustrative LPS-isolation techniques are described, for example, below in the examples section and more generally in Westphal et al., *Meth. Carbohydr. Chem.* 5:83-89, 1965, which is incorporated herein by reference in its entirety. Other LPS-isolation techniques include enzyme digestion and alcohol precipitation, chromatography by gel filtration and ion-exchange.

The isolated LPS then is subjected to mild acid hydrolysis to cleave the Lipid A from the polysaccharide or oligosaccharide domain such that the 3-deoxy-D-manno-octulosonic acid remains linked to the polysaccharide or oligosaccharide domain. Such techniques are described, for example, in Auzanneau, *J. Chem. Soc. Perkin Trans.* 1:509-516, 1991 and Rybka et al., *J. Microbiol. Methods* 64(2):171-184, 2006, both of which are incorporated herein by reference. Illustrative hydrolysis conditions include treating the LPS with acetic acid for 1-3 hours at about 100° C., or hydrolyzing LPS in a mixture of acetic acid and sodium acetate (e.g., treating 50 mg LPS with a mixture of 73.5 ml of 0.2 M acetic acid and 26.5 ml of 0.2 M sodium acetate for 5 hours at 100° C. in 5 ml volume). In some examples, the acid hydrolysis transforms the Kdo structure in the isolated LPS to an anhydro-Kdo structure.

Conjugation of the oligosaccharide or polysaccharide to the carrier protein is accomplished via formation of an oxime linkage between a carbonyl functional group present in the Kdo moiety and an aminooxy functional group present on the carrier protein. The oxime linkage reaction is a chemoselective ligation since it involves the aqueous covalent coupling of unprotected, highly functionalized biomolecules that contain at least a pair of functional groups that react together exclusively, within a biological environment. Oxime linkages can be formed in an aqueous reaction environment, and are stable, from pH 5 to pH 7. Other advantageous features of forming oxime linkages include a relatively short reaction time, a good yield, and formation at ambient temperature. These conditions avoid denaturation of the carrier protein.

The reactive carbonyl functional group present in the Kdo moiety can be an aldehyde or a ketone remaining after acid hydrolysis cleavage of the Lipid A from the LPS. The carrier protein is functionalized with an aminooxy group. The synthetic scheme for forming the oxime linkage is shown below:

Pr—Sr—O—NH$_2$+Kdo-O-SPC→Pr—Sr—O—N=C-Kdo-O-SPC   (V)

wherein Pr is a carrier protein, Sr is an optional spacer moiety, Kdo is -deoxy-D-manno-octulosonic or a derivative thereof, and OS is an oligosaccharide or polysaccharide residue from the cleavage of Lipid A from LPS. Condensation between the carbonyl and aminooxy groups leads to a stable oxime linkage between the OS and carrier protein. The spacer moiety may have any structure that is present in the linker reagents as described below. Alternatively, the Kdo-O-SPC structure could be reacted initially with an aminooxy reagent, and the resulting aminooxy-functionalized reactant could be reacted with the protein.

The oxime conjugation reaction is performed at pH 5 to about pH 7 at ambient temperature conditions in an aqueous environment. The reaction time typically ranges from about 8 to about 24 hours. However, less than 100% conjugation completion can be achieved in less than 8 hours, and the 8-24 hour reaction time assumes near 100% conjugation completion.

The carrier protein (or Kdo-O-SPC or derivitaive thereof) can be functionalized to include at least one reactive aminooxy moiety by various techniques as described, for example, in Kielb et al., *J. Org. Chem.* 70:6987-6990, 2005 and U.S. Patent Application Publication No. 2005/0169941, both of which are incorporated herein by reference. Functionalization of the carrier protein can result in the inclusion of an optional spacer moiety as noted above. In illustrative examples, a carrier protein (or Kdo-O-SPC) may be reacted with a linker reagent to incorporate the spacer moiety and the aminooxy functional moiety. The linker reagent typically is a heterobifunctional compound that includes at least one aminooxy group and a second functional group that is reactive with the carrier protein. Suitable linker reagents include aminooxy-thiol compounds. Illustrative aminooxy-thiol linker reagents include aminoooxy-alkyl-thiols such as (thiolalkyl) hydroxylamines (e.g., O-(3-thiolpropyl)hydroxylamine) and aminooxy-aryl-thiols. In the case of aminooxy-thiol linker reagents, the carrier protein may be treated to introduce thiol-reactive groups. For example, the carrier protein may be treated with a treatment agent that introduces thiol-reactive haloacetamido or thiol-reactive maleimido moieties onto the carrier protein. The haloacetamido-containing protein or maleimido-containing protein is reacted with the aminooxy-thiol reagent to form the aminooxylated carrier protein via the formation of stable thioether linkages.

The amount of oligosaccharide or polysaccharide reacted with the amount of protein may vary depending upon the specific LPS from which the O-SPC is derived and the carrier protein. However, the respective amounts should be sufficient to introduce about 5-20 chains of O-SPC onto the protein. In certain examples, the mol ratio of carbonyl groups on O-SPC) to aminooxy groups on the protein may range from about 0.3:1 to about 1:3, more particularly 1:1 to about 1:2, and more preferably about 1:1. The resulting number of oligosaccharide chains bound to a single protein carrier molecule may vary depending upon the specific LPS and the carrier protein, but in general, about 1 to about 20, such as about 1, about 2, about 3, about 4, about 5, about 6, about 7, about 8, about 9, about 10, about 11, about 12, about 13, about 14, about 15, about 16, about 17, about 18, about 19, about 20 or even more than 20 O-SPC chains can be bound to each protein carrier molecule. The yield based on the amount of protein ranges from about 70 to about 90% in protein derivatization step and about 70 to about 90% after the conjugation with the OS.

Specific, non-limiting examples of water soluble protein carriers include, but are not limited to, natural, semi-synthetic or synthetic polypeptides or proteins from bacteria or viruses. In one embodiment, bacterial products for use as carriers include bacterial wall proteins and other products (for example, streptococcal or staphylococcal cell walls), and soluble antigens of bacteria. In another embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GENBANK® Accession No. NC 007322, herein incorporated by reference), including variants that share at least 90%, at least 95%, or at least 98% amino acid sequence homology to PA, fragments that contain at least one antigenic epitope, and analogs or derivatives capable of eliciting an immune response; *B. anthracis* LF (for example, as encoded by the complement of bases 149357 to 151786 of GENBANK® Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065); *C. difficile* toxin A or toxin B (for example, as available of GENBANK® Accession No. CAA43299, AAO83645, AAO83646, CAC19891); *P. aeruginosa* exotoxin/toxoid/ (for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403,094). Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin, horseshoe crab hemocyanin, edestin, mammalian serum albumins, and mammalian immunoglobulins.

Following conjugation of the oligosaccharide or polysaccharide to the carrier protein, the conjugate can be purified by a variety of techniques well known to one of skill in the art. One goal of the purification step is to remove the unbound oligosaccharide or polysaccharide from the conjugation reaction product composition. One method for purification, involving ultrafiltration in the presence of ammonium sulfate, is described in U.S. Pat. No. 6,146,902. Alternatively, the conjugates can be purified away from unreacted oligosaccharide/polysaccharide and carrier by any number of standard techniques including, for example, size exclusion chromatography, density gradient centrifugation, hydrophobic interaction chromatography, or ammonium sulfate fractionation. See, for example, Anderson et al., *J. Immunol.* 137:1181-1186, 1986 and Jennings & Lugowski, *J. Immunol.* 127:1011-1018, 1981. The compositions and purity of the conjugates can be determined by GLC-MS and MALDI-TOF spectrometry.

B. Therapeutic Formulations.

The conjugates disclosed herein may be included in pharmaceutical compositions (including therapeutic and prophylactic formulations), typically combined together with one or more pharmaceutically acceptable vehicles and, optionally, other therapeutic ingredients (for example, antibiotics).

Such pharmaceutical compositions can be administered to subjects by a variety of mucosal administration modes, including by oral, rectal, intranasal, intrapulmonary, or transdermal delivery, or by topical delivery to other surfaces. Optionally, the conjugate can be administered by non-mucosal routes, including by intramuscular, subcutaneous, intravenous, intra-atrial, intra-articular, intraperitoneal, or parenteral routes. Alternatively, the conjugate can be administered ex vivo by direct exposure to cells, tissues or organs originating from a subject.

To formulate the pharmaceutical compositions, the conjugate can be combined with various pharmaceutically acceptable additives, as well as a base or vehicle for dispersion of the conjugate. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, TWEEN® 80), solubility enhancing agents (for example, cyclodextrins and derivatives thereof), stabilizers (for example, serum albumin), and reducing agents (for example, glutathione) can be included. Adjuvants, such as aluminum hydroxide (for example, AMPHOGEL®, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The conjugate can be dispersed in a base or vehicle, which can include a hydrophilic compound having a capacity to disperse the conjugate, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The conjugate can be combined with the base or vehicle according to a variety of methods, and release of the conjugate can be by diffusion, disintegration of the vehicle, or associated formation of water channels. In some circumstances, the conjugate is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the conjugate can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the conjugate can be brought about by including in the composition an agent which delays absorption, for example, monostearate salts and gelatin.

In certain embodiments, the conjugate can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the conjugate and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly (epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the conjugate in the required amount in an appropriate solvent with one or a combination of ingredients enumerated herein, as required, followed by filtered sterilization. Generally, dispersions are prepared by incorporating the conjugate and/or other biologically active agent into a sterile vehicle that contains a basic dispersion medium and the required other ingredients from those enumerated herein. In the case of sterile powders, methods of preparation include vacuum drying and freeze-drying which yields a powder of the conjugate plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

C. Methods of Treatment

In accordance with the various treatment methods of the disclosure, the conjugate can be delivered to a subject in a manner consistent with conventional methodologies associated with management of the disorder for which treatment or prevention is sought. In accordance with the disclosure herein, a prophylactically or therapeutically effective amount of the conjugate and/or other biologically active agent is administered to a subject in need of such treatment for a time and under conditions sufficient to prevent, inhibit, and/or ameliorate a selected disease or condition or one or more symptom(s) thereof.

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a targeted or suspected disease of condition (for example, coughing disease) as discussed herein, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure. In accordance with these methods and principles, a conjugate and/or other biologically active agent can be administered according to the teachings herein as an independent prophylaxis or treatment program, or as a follow-up, adjunct or coordinate treatment regimen to other treatments, including surgery, vaccination, immunotherapy, hormone treatment, cell, tissue, or organ transplants, and the like.

The conjugates can be used in coordinate vaccination protocols or combinatorial formulations. In certain embodiments, novel combinatorial immunogenic compositions and coordinate immunization protocols employ separate immunogens or formulations, each directed toward eliciting an anti-LPS or an anti-LOS immune response. Separate immunogens that elicit the anti-LPS or anti-LOS immune response can be combined in a polyvalent immunogenic composition administered to a subject in a single immunization step, or they can be administered separately (in monovalent immunogenic compositions) in a coordinate immunization protocol.

The administration of the conjugate of the disclosure can be for either prophylactic or therapeutic purpose. When provided prophylactically, the conjugate is provided in advance of any symptom. The prophylactic administration of the conjugate serves to prevent or ameliorate any subsequent infection. When provided therapeutically, the conjugate is provided at (or shortly after) the onset of a symptom of disease or infection. The conjugate of the disclosure can thus be provided prior to the anticipated exposure to S. sonnei so as to attenuate the anticipated severity, duration or extent of an infection and/or associated disease symptoms, after exposure or suspected exposure to the bacteria, or after the actual initiation of an infection.

For prophylactic and therapeutic purposes, the conjugate can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the conjugate can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the conjugate (for example, amounts that are effective to elicit a desired immune response or alleviate one or more symptoms of a targeted disease). In alternative embodiments, an effective amount or effective dose of the conjugate may simply inhibit or enhance one or more selected biological activities correlated with a disease or condition, as set forth herein, for either therapeutic or diagnostic purposes.

The actual dosage of the conjugate will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the conjugate for eliciting the desired activity or biological response in the subject. Dosage regimens can be adjusted to provide an optimum prophylactic or therapeutic response. As described above in the forgoing listing of terms, a therapeutically effective amount is also one in which any toxic or detrimental side effects of the conjugate and/or other biologically active agent is outweighed in clinical terms by therapeutically beneficial effects. A non-limiting range for a therapeutically effective amount of a conjugate and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight.

Upon administration of a conjugate of the disclosure (for example, via injection, aerosol, oral, topical or other route), the immune system of the subject typically responds to the immunogenic composition by producing antibodies specific for LPS, LOS and/or an antigenic epitope presented by the conjugate. Such a response signifies that an immunologically effective dose of the conjugate was delivered. An immunologically effective dosage can be achieved by single or multiple administrations (including, for example, multiple administrations per day), daily, or weekly administrations. For each particular subject, specific dosage regimens can be evaluated and adjusted over time according to the individual need and professional judgment of the person administering or supervising the administration of the conjugate. In some embodiments, the antibody response of a subject administered the compositions of the disclosure will be determined in the context of evaluating effective dosages/immunization protocols. In most instances it will be sufficient to assess the antibody titer in serum or plasma obtained from the subject. Decisions as to whether to administer booster inoculations and/or to change the amount of the composition administered to the individual can be at least partially based on the antibody titer level. The antibody titer level can be based on, for example, an immunobinding assay which measures the concentration of antibodies in the serum which bind to a specific antigen, for example, LPS and/or LOS.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

The methods of using conjugates, and the related compositions and methods of the disclosure, are useful in increasing resistance to, preventing, ameliorating, and/or treating infection and disease caused by S. sonnei in animal hosts, and other, in vitro applications. These immunogenic compositions can be used for active immunization for prevention of infection, and for preparation of immune antibodies. The immunogenic compositions are composed of non-toxic components, suitable for infants, children of all ages, and adults.

The methods of the disclosure are broadly effective for treatment and prevention of bacterial disease and associated inflammatory, autoimmune, toxic (including shock), and chronic and/or lethal sequelae associated with bacterial infection. Therapeutic compositions and methods of the disclosure for prevention or treatment of toxic or lethal effects of bacterial infection are applicable to a wide spectrum of infectious agents. Non-lethal toxicities that will be ameliorated by these methods and compositions can include fatigue syndromes, inflammatory/autoimmune syndromes, hypoadrenal syndromes, weakness, cognitive symptoms and memory loss, mood symptoms, neurological and pain syndromes and endocrine symptoms. Any significant reduction or preventive effect of the conjugate with respect to the foregoing disease condition(s) or symptom(s) administered constitutes a desirable, effective property of the subject composition/method of the disclosure.

The instant disclosure also includes kits, packages and multi-container units containing the herein described pharmaceutical compositions, active ingredients, and/or means for administering the same for use in the prevention and treatment of bacterial diseases and other conditions in mammalian subjects. Kits for diagnostic use are also provided. In one embodiment, these kits include a container or formulation that contains one or more of the conjugates described herein. In one example, this component is formulated in a pharmaceutical preparation for delivery to a subject. The conjugate is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

The subject matter of the present disclosure is further illustrated by the following non-limiting Examples.

EXAMPLES

Example 1

Growth of Bacteria and Isolation of LPS.

*S. sonnei* strain 53G and *P. shigelloides* strain 7-63 (serotype 017) were obtained from Sam Formal (Walter Reed Army Institute of Research, Silver Spring, Md.) and cultivated as described by Taylor, et al. (*Infect Immun* 61:3678-3687, 1993). LPS from either strain was extracted by the hot phenol method and purified as described by Westphal and Himmelspach (1983, *Prog Allergy* 33:9-39, incorporated herein by reference in its entirety).

Isolation of Oligosaccharides.

*S. sonnei* LPS (200 mg) was treated with 1% acetic acid at 100° C. for 1.5 hours. Lipid A was removed by ultracentrifugation at 142,000×g for 5 hours at 4° C., and the soluble product subjected to gel chromatography on a BIOGEL® P-10 (1×100 cm) column in pyridine/acetic acid/water buffer (4:8:988 mL), monitored with a Knauer differential refractometer.

Analytical Methods.

Protein concentration was measured by the method of Lowry et al. (*J Biol Chem* 193:265-275, 1951), and sugar concentration was measured by the anthrone assay (Scott and Melvin, *Anal Chem* 25:1656-1661, 1953). SDS/PAGE used 14% gels according to the manufacturer's instructions (BIO-RAD®). Immunodiffusion was performed in 1% agarose in phosphate buffered saline (PBS).

Spectroscopy.

$^1$H and $^{13}$C NMR spectra were recorded by using a Varian Inova 500-MHz spectrometer for samples in $D_2O$ solutions at 35° C. with acetone standard (2.225 ppm for $^1$H and 31.5 ppm for $^{13}$C) using standard pulse sequence COSY, TOCSY (mixing time 120 ms), NOESY (mixing time 200 ms), and Heteronuclear Single Quantum Coherence and Heteronuclear Multiple Bond Correlation (100-ms long range transfer delay). Capillary electrophoresis (CE)-MS was obtained on a 4000 QTRAP mass spectrometer (Applied Biosystems/MDS Sciex) with a Prince CE system (Prince Technologies) with a 90-cm length bare fused-silica capillary using 15 mM ammonium acetate in deionized water, pH 9.0, as an injection module. A sheath solution (isopropanol/methanol, 2:1) was delivered at a flow rate of 1.0 µL/min. A 5-kV electrospray ionization voltage was used for negative ion detection modes. For some experiments samples were dephosphorylated at 1 mg/mL of 40% hydrofluoric acid (HF) for 24 hours at 4° C. MALDI-TOF mass spectra of the derivatized proteins and the conjugates were obtained with an OmniFlex MALDI-TOF instrument (Bruker Daltonics) operated in the linear mode. Samples for analysis were desalted, and 1 µL was mixed with 20 µL of sinnapinic acid matrix made in 30% $CH_3CN$ and 0.1% trifluoroacetic acid. Next, 1 µL of mixture was dried on the sample stage and placed in the mass spectrometer.

Preparation of Conjugates.

To 15 mg of Bovine Serum Albumin (BSA) (Sigma) or recombinant Diphtheria Toxin (rDT) [CRM H21G (Schneerson et al., *J Exp Med* 152:361-376, 1980)] in 2.2 mL of buffer A (PBS, 0.1% glycerol, 5 mM ethylendiaminetetraacetic acid (EDTA), pH7.2), 4 mg of N-succinimidyl 3-(bromoacetamido)propionate (SBAP; Pierce) in 40 µL of DMSO was added and reacted at pH 7.2 in room temperature with mixing for 1.5 hours. Next, the solution was applied to a SEPHADEX™ G-50 column (1×50 cm) in PBS, and the void volume fraction (Pr—Br) was concentrated by using an Amicon Ultra-15 centrifuge filter device (MILLIPORE®) to 2.6 mL (13 mg recovered), and 0.1 mL was removed for analysis. To 12 mg of Pr—Br in 2.4 mL of buffer A, 10 mg of O-(3-thiopropyl)hydroxylamine was added in 300 µL of 1 M KCl and reacted at pH 7.2 in room temperature with mixing for 3 hours. Next, the solution was passed through the SEPHADEX® G-50, and the void volume fraction (Pr—$ONH_2$) was concentrated to 2.6 mL as above, and 0.2 mL was removed for analysis. Ten milligrams of Pr—$ONH_2$ was reacted with 25 mg (7.8 µmol) O-SPC in 3 mL of buffer A overnight, at pH 7.2, in room temperature with mixing. The solution was then passed through the SEPHAROSE® G-75 (1×100 cm) in PBS, and the void volume fraction was collected and analyzed for sugar and protein contents and molecular mass by MALDI-TOF and SDS/PAGE. Three conjugates were obtained this way: 1, BSA/O-SPC-F2; 2, rDT/O-SPC-F2; and 4, BSA/O-SPC-F3. For preparation of conjugate 3, binding of rDT-$ONH_2$ and O-SPC-F2 was done in 1.5 mL of buffer A, and the product (rDT/O-SPC-F2) contained twice the number of O-SPC-F2 chains per rDT molecule as conjugate 2 (12 vs. 6). Conjugates of full-length O-SP bound by multiple attachments to either recombinant *Bacillus anthracis* protective antigen or rEPA were prepared as described by Passwell, et al., *Pediatr Inf Dis J* 22:701-706, 2003).

Immunization.

Five- to 6-week-old female National Institutes of Health Swiss—Webster mice were injected subcutaneously (s.c.) 3 times at 2-week intervals with 2.5 µg of saccharide as a conjugate in 0.1 mL of PBS. Groups of 10 mice were exsanguinated 7 days after the second or third injections as described by Schneerson et al. *J Exp Med* 152:361-376, 1980. Controls received PBS.

Antibodies.

Serum IgG antibodies were measured by ELISA using *S. sonnei* or *P. shigelloides* LPS as a coating antigen as described by Plikaytis and Carlone, 2005, *Program ELISA for Windows User's Manual* (Centers for Disease Control, Atlanta, Version 2). The results were computed with an ELISA data processing program provided by the Biostatistics and Information Management Branch, Centers of Disease Control, Atlanta (Johnson and Nicholls, 1994, *J Biol Chem* 269:4349-4354). A polyclonal rabbit antiserum obtained by immunizing rabbits with multiple intravenous (i.v.) injections of heat-killed *S. sonnei* bacteria was used in the immunodiffusion assays.

Competitive Inhibition ELISA.

Inhibition was assayed by incubating conjugate induced mice sera, diluted to the concentration that gave an absorbance of $\mu$ 1.0 at a wavelength of 405 nm (A405), with 2, 10, or 50 µg of inhibitor (Table 2) per well, for 1 hour at 37° C. and overnight at 4° C. The ELISA was then continued as usual. Sera at the same dilution with and without inhibitor were compared. Percentage inhibition was defined as (A405 adsorbed serum/A405 nonadsorbed serum) X 100%. Core-free *P. shigelloides* O-SP was obtain by treating the O-SP with anhydrous HF for 1 hour at 25° C. *Haemophilus influenzae* type a capsular polysaccharide was used as a control.

Statistics.

GMvalues of the groups of 10 mice were calculated. Unpaired t test was used to compare GMs between different groups of mice.

Isolation and Chemical Characterization of O-SPC.

Figure 2:
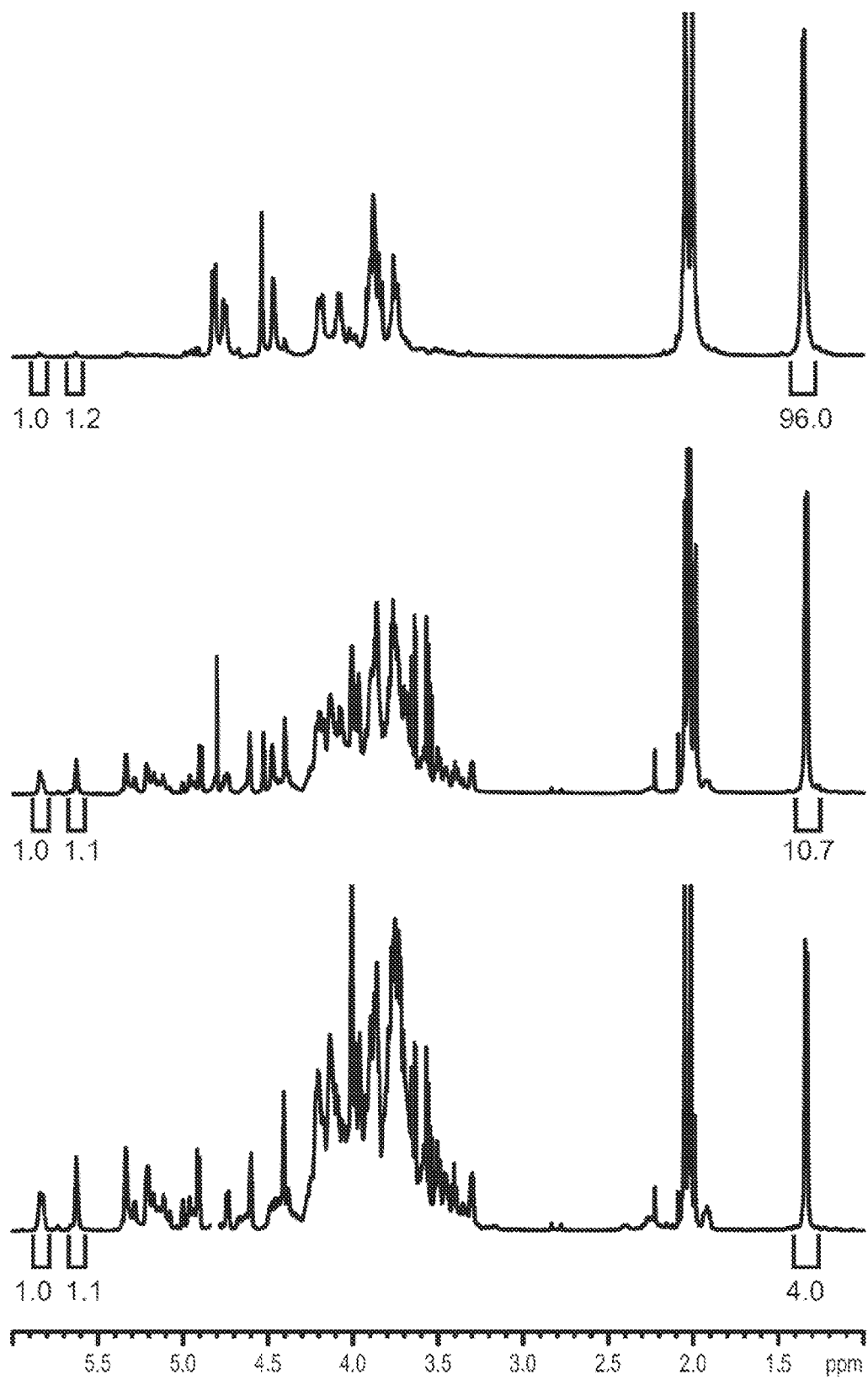
FIG. 2 is a one dimensional proton nuclear magnetic resonance (NMR) spectrum of *S. sonnei* O-SP. Integration of the $^1$H NMR spectra of *S. sonnei* O-SP (Top), O-SPC-F2 (Middle), and O-SPC-F3 (Bottom) for the determination of the number of RU attached to the core oligosaccharide of *S. sonnei*. Signals at 5.82 and 5.62 ppm belonging to core α-GalM and α-GalL (1 proton) were integrated with signals at 1.34-1.36 ppm belonging to FucNAc4N methyl group (3 protons) of O-SP (see Table 3).
Figure 4:
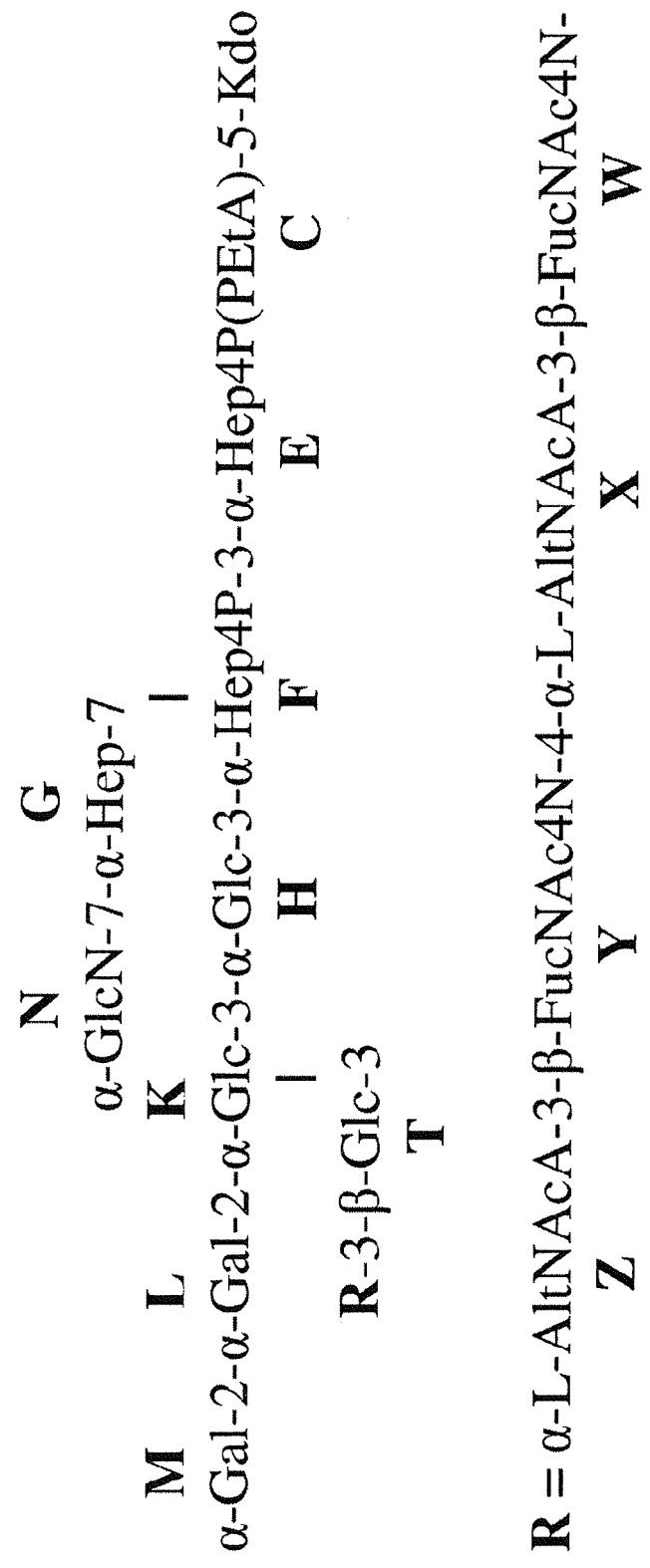
FIG. 4 is a LPS structure of *S. Sonnei* referred to herein as scheme 1.

LPS was extracted from 18-hour cultures of *S. sonnei* or *Plesiomonas shigelloides* as described by Taylor, et al., (*Infect Immun* 61:3678-3687, 1993). *S. sonnei* saccharides, released after mild acid hydrolysis from lipid A, were separated into 4 fractions (FIG. 1). The yields of fractions 1-4 were 50%, 17%, 31%, and 2% by weight, respectively. Integration of the FucNAc4N methyl signal in 1H-NMR spectra (1.34-1.36 ppm) relative to the anomeric signals of core $\alpha$-Gal M (5.82 ppm) and $\alpha$-Gal L (5.62 ppm) (see Table 1 and FIG. 4 Scheme 1) showed that fraction F1 contained core with $\approx$29 O-SP repeat units (RU), F2 contained core with an average of 3.5 RU, and F3 contained core with an average of 1.3 RU (FIG. 2). Fraction F4 contained various degradation products and was not studied further.

Figure 3A:
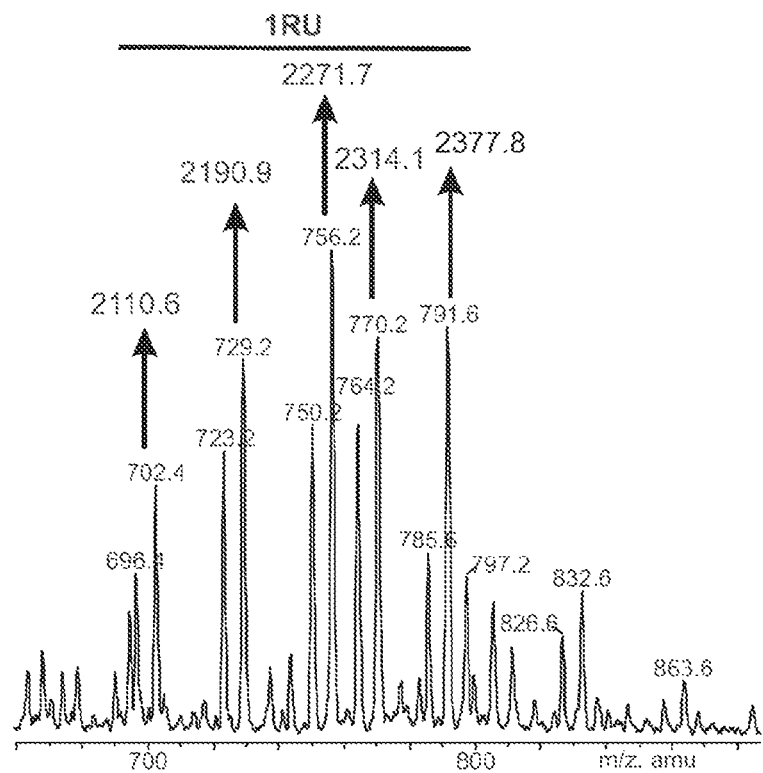
FIGS. 3A and 3B are electrospray ionization (ESI) mass spectra of *S. sonnei* O-SPC-F3 (FIG. 3A) and dephosphorylated O-SPC-F2 (FIG. 3B). Triple charged ions are shown. Components of fraction 2 (F2) with masses of 2514.3 and 2918.1 Daltons (Da) contain one phosphate because of incomplete dephosphorylation. Assignments of molecular masses are in given below in the Examples section.

MS spectra confirmed that fraction F3 consisted of the core with 1 RU (FIG. 3A). The following species have been detected: core+1 RU without the core GlcN (2,110.6 Da), core+1 RU including GlcN (2,271.7 Da), core+1 RU including GlcN but without phosphate (P) (2,190.9 Da), core+1 RU with GlcN, P and PEtN (2,377.8 Da), and the latter but without P (2,314.1 Da).

Figure 3B:
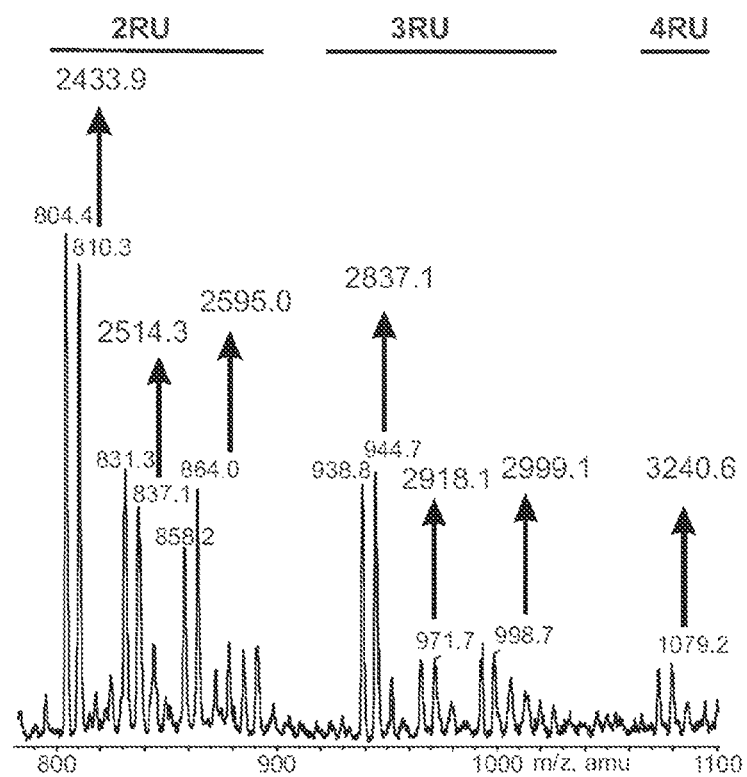

MS analysis of fraction F2 showed a complex spectrum containing 3x, 4x, and 5x charged ions of the oligosaccharides with 2, 3, and 4 RU, heterogenic in P, PEtN, and GlcN substitutions, respectively. To interpret the spectrum, F2 was partially dephosphorylated. The following species were detected (FIG. 3B): (i) core+2 RU (2,433.9 Da), and partially substituted with P (2,496.9 Da), and core+2 RU with GlcN (2,595.0 Da); (ii) core+3 RU (2,837.1 Da), and partially substituted with a phosphate group (2,918.1 Da), or core+2 RU with GlcN (2,999.1 Da); and (iii) core+4 RU (3,240.6 Da). Integration of NMR data indicated that even longer oligosaccharides, with 5 RU were present in F2 but their signals were not observed in the mass spectra, probably because they showed multiply-charged ions mixed with background signals. The F2 and F3 oligosaccharide fractions were used for conjugation.

Preparation and Characterization of Conjugates.

Three conjugates were prepared by binding O-SPC-F2 to either BSA (conjugate 1; BSA/O-SPC-F2) or recombinant diphtheria (rDT) toxin (conjugates 2 and 3: rDT/O-SPC-F2). One conjugate was prepared by binding O-SPC-F3 to BSA (conjugate 4: BSA/OSPC-F3).

The conjugation was based on formation of stable oxime linkages between the Kdo residue present at the O-SPC reducing end and an aminooxy linker bound to the carrier protein. This procedure yielded high molecular mass conjugates, revealed by MALDI-TOF MS, SDS/PAGE, and protein and sugar colorimetric assays; all methods provided comparable results. The number of O-SPC chains per protein was calculated from the molecular mass of the conjugate, the carrier protein, and the O-SPC. Thus, conjugate 1 contained +7 O-SPC chains/BSA molecule, conjugate 2 contained +6 O-SPC/rDT, conjugate 3 contained +12 O-SPC chains/rDT, and conjugate 4 contained +11 O-SPC chains/BSA (Table 2). An excess of saccharide was used for conjugation to ensure maximal binding. The yield of the protein in the conjugate was 65-75%, and the yield of the saccharide was 30-35%. Conjugates 1, 2, and 3 prepared with O-SPC-F2 reacted by double immunodiffusion with rabbit anti-*S. sonnei* and anti-protein sera by a line of identity. Conjugate 4 prepared with O-SPC-F3 precipitated with the anti-BSA serum but not with the anti-*S. sonnei* serum. Only conjugates of O-SPC-F2 were used for immunization.

IgG Anti-LPS Responses (Table 2).

Conjugates 1, 2, and 3 elicited low levels of IgG anti-LPS after the second injection with a booster response after the third. The geometric means (GM) of IgG anti-LPS after the third injection were 366 ELISA units (EU) for conjugate 1 and 392 EU for conjugate 2. Conjugate 3, which contained twice as much of O-SPC-F2 chains per rDT than conjugate 2 (12 vs. 6), induced statistically-lower GM antibody levels (150 EU vs. 392 EU; P<0.01). All 3 O-SPC-F2 conjugates induced statistically-higher antibody levels than the "lattice"-type conjugate (a clinical lot) prepared with the full-length O-SP (366 vs. 67, P<0.0001; 392 vs. 67, P<0.0001; 150 vs. 67: P<0.05).

IgG Anti-O-SP Responses (Table 3).

Coating the ELISA plates with *S. sonnei* or *P. shigelloides* LPS of identical O-SP but different sera induced by either O-SPC or O-SP conjugates were inhibited similarly by O-SPs of *S. sonnei* and of *P. shigelloides* with or without the core.

IgG Anti-O-SP Responses (Table 4).

Coating the ELISA plates with *S. sonnei* or *P. shigelloides* LPS of identical O-SP but different sera induced by either O-SPC or O-SP conjugates were inhibited similarly by O-SPs of *S. sonnei* and of *P. shigelloides* with or without the core.

Example 3

Treatment of Subjects with *S. sonnei* O-PS Conjugate

This example describes methods that can be used to treat a subject that has or is at risk of having an infection from *S. sonnei* by administration of one or more of the disclosed conjugates. In particular examples, the method includes screening a subject having, thought to have, or at risk of having (for example due to impaired immunity, physiological status, or exposure to *S. sonnei*) a *S. sonnei* infection. Subjects of an unknown infection status can be examined to determine if they have an infection, for example using serological tests, physical examination, enzyme-linked immunosorbent assay (ELISA), radiological screening or other diagnostic technique known to those of skill in the art. In some examples, a subject is selected that has a *S. sonnei* infection or is at risk of acquiring a *S. sonnei* infection. Subjects found to (or known to) have a *S. sonnei* infection and thereby treatable by administration of the disclosed conjugates are selected to receive the conjugates peptide. Subjects may also be selected who are at risk of developing a *S. sonnei* infection for example, the elderly, the immunocompromised and the very young, such as infants.

Subjects selected for treatment can be administered a therapeutic amount of disclosed conjugate. The conjugate can be administered at doses of 1 μg/kg body weight to about 1 mg/kg body weight per dose, such as 1 μg/kg body weight-100 μg/kg body weight per dose, 100 μg/kg body weight-500 μg/kg body weight per dose, or 500 μg/kg body weight-1000 μg/kg body weight per dose or even greater. However, the particular dose can be determined by a skilled clinician. The agent can be administered in several doses, for example continuously, daily, weekly, or monthly.

The mode of administration can be any used in the art. The amount of agent administered to the subject can be determined by a clinician, and may depend on the particular subject treated. Specific exemplary amounts are provided herein (but the disclosure is not limited to such doses).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An immunogenic conjugate comprising the structure of:

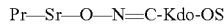
Pr—Sr—O—N=C-Kdo-OS wherein Pr is a carrier protein, Sr is an optional spacer moiety, Kdo is 3-deoxy-D-manno-octulosonic acid, and OS comprises at least one oligosaccharide or polysaccharide obtained from *S. sonnei*.

2. The immunogenic conjugate of claim 1, wherein the oligosaccharide or polysaccharide includes a core oligosaccharide.

3. The immunogenic conjugate of claim 2, wherein the oligosaccharide core, comprises:

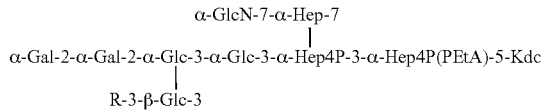

α-GlcN-7-α-Hep-7
|
α-Gal-2-α-Gal-2-α-Glc-3-α-Glc-3-α-Hep4P-3-α-Hep4P(PEtA)-5-Kdc
|
R-3-β-Glc-3 wherein R is between 1 and 10 disaccharide repeat units.

4. The immunogenic conjugate of claim 3, wherein the oligosaccharide core, consists of:

(II)

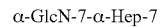
α-GlcN-7-α-Hep-7
|
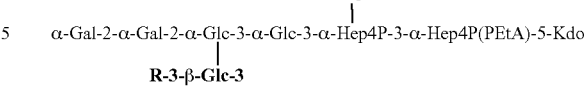
α-Gal-2-α-Gal-2-α-Glc-3-α-Glc-3-α-Hep4P-3-α-Hep4P(PEtA)-5-Kdo
|
R-3-β-Glc-3 wherein R is between 1 and 10 disaccharide repeat units.

5. The immunogenic conjugate of claim 3, wherein the disaccharide repeat unit comprises:

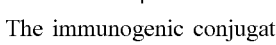
α-L-AltNAcA-3-β-FucNAc4N-4-.

6. The immunogenic conjugate of claim 5, wherein the disaccharide repeat unit consists of:

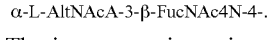
α-L-AltNAcA-3-β-FucNAc4N-4-.

7. The immunogenic conjugate of claim 5, wherein the conjugate consists of 1-10 disaccharide repeat units.

8. The immunogenic conjugate of claim 5, wherein the conjugate comprises 3-5 disaccharide repeat units.

9. The immunogenic conjugate of claim 1, wherein the conjugate comprises between 1 and 20 oligosaccharides per carrier protein molecule.

10. The immunogenic conjugate of claim 9, wherein the conjugate comprises between 1 and 14 oligosaccharides per carrier protein molecule.

11. The immunogenic conjugate of claim 1, wherein the protein carrier comprises recombinant diphtheria toxin (rDT).

12. The immunogenic conjugate of claim 1, wherein the protein carrier comprises recombinant *Pseudomonas aeruginosa* Exoprotein A (rEPA).

13. The immunogenic conjugate of claim 1, wherein the protein carrier comprises recombinant *C. difficile* toxin B repeat (rBRU).

14. A therapeutic composition comprising the conjugate of claim 1 and a pharmaceutically acceptable carrier.

15. A method of eliciting an immune response in a subject, comprising administering to the subject the immunogenic conjugate of claim 1.

16. A method of treating and/or inhibiting an infection by *S. sonnei* in a subject, comprising:
administering to the subject the immunogenic conjugate of claim 1.

17. A therapeutic composition comprising the conjugate of claim 8 and a pharmaceutically acceptable carrier.

18. A method of treating and/or inhibiting an infection by *S. sonnei* in a subject, comprising:
administering to the subject the immunogenic conjugate of claim 8.

19. The immunogenic conjugate of claim 8, wherein the conjugate comprises between 1 and 14 oligosaccharides per carrier protein molecule.

* * * * *